United States Patent [19]
Marquis et al.

[11] Patent Number: 6,156,160
[45] Date of Patent: Dec. 5, 2000

[54] ALKYLENE CARBONATE PROCESS

[75] Inventors: Edward T. Marquis, Austin; Mercy Mathai Varghese, Houston, both of Tex.

[73] Assignee: Huntsman Petrochemical Corporation, Austin, Tex.

[21] Appl. No.: 09/167,361

[22] Filed: Oct. 7, 1998

[51] Int. Cl.[7] ........................... B01D 3/00; C07D 317/36
[52] U.S. Cl. ............................... 203/29; 159/49; 203/72; 203/74; 203/80; 203/77
[58] Field of Search .................... 203/29, 72, 73, 203/74, 78, 77, 80, DIG. 6; 549/230; 159/49, 6.2, 13.1, 13.2

[56] References Cited

U.S. PATENT DOCUMENTS

| | | |
|---|---|---|
| 1,907,891 | 5/1933 | Steimmig et al. . |
| 2,773,070 | 12/1956 | Lichtenwaler et al. ................. 549/230 |
| 4,233,221 | 11/1980 | Raines et al. . |
| 4,314,945 | 2/1982 | McMullen et al. . |
| 4,519,875 | 5/1985 | Becker et al. ............................ 203/29 |
| 4,877,886 | 10/1989 | Ream . |
| 4,952,542 | 8/1990 | Ream . |
| 5,391,767 | 2/1995 | Mais et al. . |

FOREIGN PATENT DOCUMENTS 0 540 225   10/1992   European Pat. Off. .

OTHER PUBLICATIONS

Noyes, W. Albert, Jr., Editor, "The Journal of the American Chemical Society" vol. LXXV; pp. 1263–1264; Jan.–Mar. 1953.

International Search Report, Apr. 13, 1999.

Peppel, W. J., "Preparation and Properties of the Alkylene Carbonates," *Industrial and Engineering Chemistry*, vol. 50(5) 767–770, May 1958.

*Primary Examiner*—Virginia Manoharan
*Attorney, Agent, or Firm*—O'Keefe, Egan & Peterman, LLP

[57] ABSTRACT

This invention concerns a process to provide high purity alkylene carbonate though use of multiple distillations wherein the unused fractions are recycled to the reactor.

12 Claims, 2 Drawing Sheets

ALKYLENE CARBONATE PROCESS

BACKGROUND OF INVENTION

This invention concerns a method for the production of alkylene carbonate, especially high purity alkylene carbonate.

Alkylene carbonates are well known materials that have been produced commercially for decades. Alkylene carbonate may be manufactured by a variety of methods. One such method is described in U.S. Pat. No. 2,773,070 (1956). Some applications of alkylene carbonate demand use of very high purity products. For example, when alkylene carbonates are used as solvents for electrolyte salts in lithium batteries, the alkylene carbonate preferably contain essentially no impurities (e.g., glycol less than 20 parts per million ("ppm")) and very low water amounts (also less than 20 ppm). In the past, such purification was accomplished, for instance, by treatment by distillation; however, the impure streams from the distillation tower(s), which may constitute up to 50 percent of the effluent from the carbonate reactor, are typically considered useless by-products that are destroyed. The present inventors have recognized that a need exists to remedy this wasteful practice and to provide a more economical process. The present inventors have also recognized that a need exists for high purity alkylene carbonate on a commercial scale.

SUMMARY OF INVENTION

The present invention provides a solution to one or more of the disadvantages and deficiencies described above.

In one broad respect, this invention is a process useful for the manufacture of alkylene carbonate, comprising: contacting carbon dioxide, an alkylene oxide, and a carbonation catalyst in a reaction zone to produce a crude reactor effluent; subjecting the crude reactor effluent to low temperature evaporation to form an evaporator overhead containing alkylene carbonate and an evaporator bottoms stream containing the catalyst, and recycling the evaporator bottoms stream to the reaction zone, removing any light components present in the evaporator overhead to form a second evaporator overhead and recycling the light components to the reaction zone; distilling the second evaporator overhead to form a first distillation overhead stream and a first distillation bottoms stream containing alkylene carbonate, and recycling the first distillation overhead stream to the reaction zone; distilling the first distillation bottoms stream to form a second distillation overhead stream and a second distillation bottoms stream and recycling the second distillation bottoms stream to the reaction zone; distilling the second distillation overhead stream to form a third distillation overhead stream and a third distillation bottoms stream and recycling the third distillation overhead stream to the reaction zone; distilling the third distillation bottoms stream to form a fourth distillation overhead stream containing purified alkylene carbonate and a fourth distillation bottoms stream, and recycling the fourth distillation bottoms stream to the reaction zone.

In another broad respect, this invention is a process useful for the manufacture of alkylene carbonate, comprising: distilling a first stream containing an alkylene carbonate in a purity of about 99 percent or more to form a first bottoms stream containing alkylene carbonate at a purity greater than the purification stream and an first overhead stream containing alkylene carbonate at a purity greater than the purification stream, and introducing the first overhead stream to an alkylene carbonate reactor; distilling the first bottoms stream to form a second overhead stream containing high purity alkylene carbonate and a second bottoms stream, and recycling the second bottoms stream to the alkylene carbonate reactor.

In another broad respect, this invention is process useful for the manufacture of alkylene carbonate, comprising: contacting carbon dioxide, an alkylene oxide, and a carbonation catalyst in a reactor to produce a crude reactor effluent; subjecting the crude reactor effluent to low temperature evaporation to form an evaporator overhead containing alkylene carbonate and an evaporator bottoms stream containing the catalyst, and recycling the evaporator bottoms stream to the reactor, removing any light components present in the evaporator overhead to form a second evaporator overhead and recycling the light components to the reactor; distilling the second evaporator overhead to form a first distillation overhead stream and a first distillation bottoms stream containing alkylene carbonate, and recycling the first distillation overhead stream to the reactor; distilling the first distillation bottoms stream to form a second distillation overhead stream and a second distillation bottoms stream and recycling the second distillation bottoms stream to the reactor; distilling the second distillation overhead stream in a distillation column to form a third distillation overhead stream, a high purity middle fraction having a purity of at least 99.99% and a third distillation bottoms stream, withdrawing the middle fraction from the column, and recycling the third distillation overhead stream and the third distillation bottoms stream to the reactor.

In yet another broad respect, this invention is a process useful for the manufacture of ethylene carbonate, comprising: contacting carbon dioxide, an ethylene oxide, and a carbonation catalyst in a reactor to produce a crude reactor effluent; subjecting the crude reactor effluent to low temperature evaporation to form an evaporator overhead containing ethylene carbonate and an evaporator bottoms stream containing the catalyst, and recycling the evaporator bottoms stream to the reactor, removing any light components present in the evaporator overhead to form a second evaporator overhead and recycling the light components to the reactor; subjecting the second evaporator overhead to a second low temperature evaporation to form a less pure fraction and a more pure fraction, and recycling the less pure fraction to the reactor; and either: (1) distilling the more pure fraction in a distillation column to form a less pure overhead fraction, a high purity middle fraction having a purity of at least 99.99% and a less pure bottoms fraction, withdrawing the middle fraction from the column, and recycling the less pure overhead fraction and the less pure bottoms fraction to the reactor, or (2) distilling the more pure fraction to form a distillation overhead stream and a distillation bottoms stream and recycling the distillation overhead stream to the reactor; distilling the distillation bottoms stream to form a second distillation overhead stream containing purified alkylene carbonate having a purity of at least 99.99% and a second distillation bottoms stream, and recycling the second distillation bottoms stream to the reactor.

This invention has a number of advantages. For example, high purity alkylene carbonate may be produced more cost-effectively as compared to existing practices. The process of this invention, furthermore, generates less waste and higher yields than existing processes. Advantageously, this process may be implemented using conventional equipment.

DETAILED DESCRIPTION OF THE INVENTION

Figure 1:
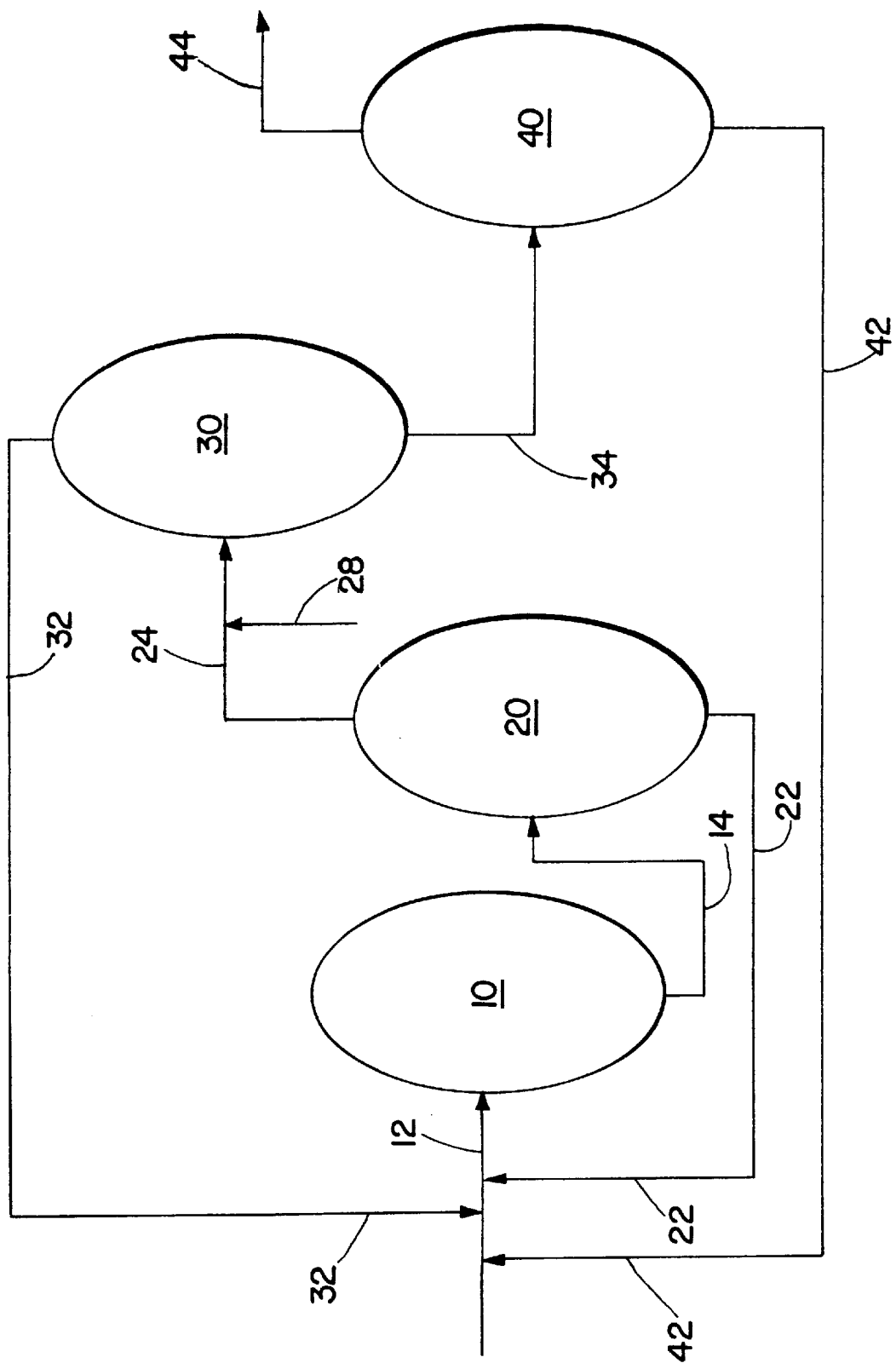
FIG. 1 shows a representative process scheme for the practice of this invention.

In FIG. 1 there is shown a representative configuration for the practice of this invention. The starting reactants for production of alkylene carbonate, alkylene oxide and carbon dioxide, are introduced into the carbonate reactor 10 via line 12. It should be appreciated that while lines and conduits are depicted in FIG. 1, such liens and conduits need not be present and the effluents may be conveyed between apparatuses and method.

In accordance with this invention, alkylene oxides may be reacted in the reactor 10 with carbon dioxide in the presence of ammonium halides having the formula

Where X is any halide ion, and $R_1$, $R_2$, $R_3$, and $R_4$ may each be hydrogen, alkyl, aryl, alkenyl, alkaryl, or aralkyl in any combination or in which any two of the radicals $R_1$, $R_2$, $R_3$ and $R_4$ may be interconnected to form with the basic nitrogen atom a ring of the pyridine, piperidine, pyrollidine, pyrroline, morpholine, or thiomorpholine series. In certain embodiments, the alkyl group may contain from 1 to 20 carbon atoms, the aryl group may be phenyl or naphthyl, the alkenyl group may contain from 2 to 20 carbon atoms, the alkaryl group may be an alkyl substituted phenyl or naphthyl in which the alkyl group may contain from 1 to 4 carbon atoms and the aralkyl group may be an alkyl group that may contain from 1 to 4 carbon atoms substituted by a phenyl or naphthyl radical.

The alkylene oxides which may be employed in the reaction arc those of the oxirane system. Preferably, the alkylene oxides employed have a structural formula

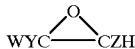

in which W, Y, and Z may be hydrogen, or the groups alkyl containing from 1 to 20 carbon atoms, aryl containing from 6 to 12 carbon atoms, cycloalkyl containing from 5 to 20 carbon atoms, alkenyl containing from 2 to 20 carbon atoms, or in which any two of the groups W, Y, and Z may be interconnected to form with the two carbon atoms shown in the formula a carbocyclic ring. Ethylene oxide, propylene oxide and butylene oxide are representative examples of such alkylene oxides.

The reaction may be carried out at a temperature of from about 100 degrees Centigrade to about about 225 degrees Centigrade, preferably from about 175 degrees Centigrade to about 215 degrees Centigrade, and under a pressure of more than about 300 pounds per square inch gauge, preferably from about 1,000 to about 3,000 pounds per square inch gauge. The reaction may be conducted either batchwise or continuously. For example, the catalyst may be continuously introduced in solution form along with the alkylene oxide and the carbon dioxide under desired pressure into one end of a reaction vessel and the products of reaction continuously withdrawn from the other end. A preferred solvent for the catalyst is the alkylene carbonate reaction product or a tertiary alcohol, e.g., tertiary butyl or amyl alcohol. Alternatively, batches of the alkylene oxide and the catalyst may be introduced into an autoclave or bomb type of reactor, the desired pressure built up by introducing carbon dioxide and the reaction mixture agitated while being heated to the reaction temperature and maintained under a superatomospheric pressure of carbon dioxide. Irrespective of whether a batch or continuous procedure is followed, each unit weight of reactants and reaction products resulting therefrom is maintained at reaction temperature and pressure for from about 1 to about 90 minutes, preferably from about 30 to about 60 minutes. This time interval is referred to herein as the reaction time.

The alkylene oxide and carbon dioxide are mixed in proportions to provide an excess of carbon dioxide over and above the stoichiometric amount required for reaction. This excess may be of the order of from 1% to 500% by weight.

The ammonium halide may be obtained as such from any available source or produced in any desired manner. While ammonium iodides, bromides, chlorides, and fluorides are all of them effective in catalyzing the synthesis of alkylene carbonates from alkylene oxides and $CO_2$, the iodides and bromides are generally considered to be more effective than the chlorides and fluorides. It is preferred to use the bromides since they are highly effective and in addition are much more stable under conditions of use than are the iodides, which tend to decompose on heating with evolution of elemental iodine which poses an additional purification problem. The ammonium radical may be unsubstituted $(NH_4)^+$ or mono-, di-, tri-, or tetrasubstituted. Preferably, a tetrasubstituted ammonium halide is employed.

Representative examples of preferred catalysts include but are not limited to tetraethyl ammonium bromide, tetramethyl ammonium bromide, benzyltriethyl ammonium bromide and tetrabutyl ammonium bromide. These catalysts may easily be produced by heating a tertiary amine with an alkyl bromide. Thus, from triethyl amine and benzyl bromide, benzyltriethyl ammonium bromide is obtained. The ammonium halide catalysts may be purified by crystallization from a suitable solvent: in most cases an alcohol may be used for this purification. Methyl and ethyl alcohols are satisfactory for this purification in the case of most ammonium halides; however, a preferred solvent for tetraethylammonium bromide is tertiary butyl alcohol in which the catalyst is almost completely insoluble at room temperature, but in which it is quite soluble near the boiling point. Tertiary amyl alcohol is similarly well suited for this use.

The amount of catalyst used in general should be from 0.1% to 10%, preferably from about 1 to about 5% based on the weight of the reaction mixture. In general, the greater the catalyst concentration, within these limits, the more rapid and complete the reaction.

The carbonate reactor may be operated as described in U.S. Pat. No. 2,773,070 and W. J. Peppel, "Preparation and Properties of the Alkylene Carbonates," Industrial and Engineering Chemistry, Volume 50, Number 5, May, 1958. The reactor 10 may be of conventional design as is currently being used in industry for this reaction.

The crude reactor effluent from reaction 10 may be conveyed via line 14 to an evaporation apparatus 20. The evaporation apparatus 20 may be of conventional design and is operated such that a low residence time is maintained to minimize degradation of the catalyst at high temperatures. The bottoms from the evaporator 20 contain inter alia, the catalyst. The overhead contains alkylene product and lights. The evaporator may be, for example, a wiped film evaporator or falling film tower. Typically, the evaporator is operated at a temperature from about 50 to about 150, and at a pressure of form about 0.1 to about 100. If the catalyst is not sensitive to high temperatures, it may not be necessary to employ an evaporator having low residence time. The bottoms may be recycled to the reactor 10 via conduit 22. Typically, the evaporator splits the material such that about 5 to about 20 percent exit as bottoms, with about 80 to about 95 percent being overhead. The alkylene product stream exiting the evaporator usually has a purity in the range of about 98 to about 99.5. Optionally, a second evaporator may be employed in series, again with the less pure fractions being returned to the reactor.

Optionally, the effluent from reactor 10 may be sent to a finishing drum, not shown. After removing lights from the evaporator overhead (using for instance a low pressure separator and/or a gas-liquid separator), the overhead is sent, directly or indirectly, to a first distillation tower 30 via line 24. The product may for example be sent to a storage unit prior to distillation. The first distillation tower, and all distillation towers used herein, serve to further purify the alkylene carbonate. The first distillation tower may be operated at any temperature and pressure which will afford a first distillation bottoms that is a higher purity than the alkylene carbonate received from the evaporator. In general, the first distillation tower is operated at a temperature of from about 50 degrees Centigrade to about 150 degrees Centigrade and a pressure of from about 0.1 to about 100 mm Hg.

The overhead from the first distillation tower may be recycled to reactor 10 via line 32. The first distillation bottoms, which constitutes about 90 to about 99 percent of the material fed to the first distillation tower, exits the first tower 30 via conduit 34, and is transferred to the second distillation tower 40.

In second distillation tower 40, the first distillation bottoms is subjected to additional purification. The second distillation bottoms may be recycled to the reactor 10 via conduit 42. The purified alkylene carbonate exits the second tower 40 via line 44. The purity of the alkylene carbonate stream exiting the second distillation column is usually in the range from about 99.5 99.95 to about 99.95 percent.

To achieve even further purification, the second distillation overhead is then subjected to two additional distillations. The additional distillations may be accomplished in a variety of ways. For example, the second distillation overhead may be stored and reintroduced into first distillation tower 30 via line 28. This would be done when the reactor 10 and evaporator 20 were not running. The overhead from the first distillation tower 30 and bottoms from the second distillation tower 40 would again be recycled to reactor 10. This recycling provides many advantages. The most important advantages are conservation of mass, which provides a high overall yield, and a cost advantage as contrasted against processes where such overhead and bottoms destroyed or not used to make additional high purity alkylene carbonate.

In another alternative, the second distillation overhead is sent to another tower or towers different from the towers 30 and 40 shown in FIG. 1. For example, the overhead may be sent to a single, very large tower instead of two smaller towers in series. The larger tower may have 50 to 150 theoretical plates containing for instance 100 trays and packing, as opposed to smaller towers having 40 to 60 trays. In this case, the middle fraction from the large tower is the high purity alkylene carbonate, with the overhead and bottoms being recycled to the reactor 10. Hence, recycling of fractions to the reactor 10 would still be performed even if a single tower were used or if the effluent was sent to other towers, off-site or otherwise, for further purification. It should be appreciated that an important aspect of this invention is the return of the less pure fractions to the reactor, which leads to higher yields, less waste and a more economical high purity alkylene carbonate process.

Figure 2:
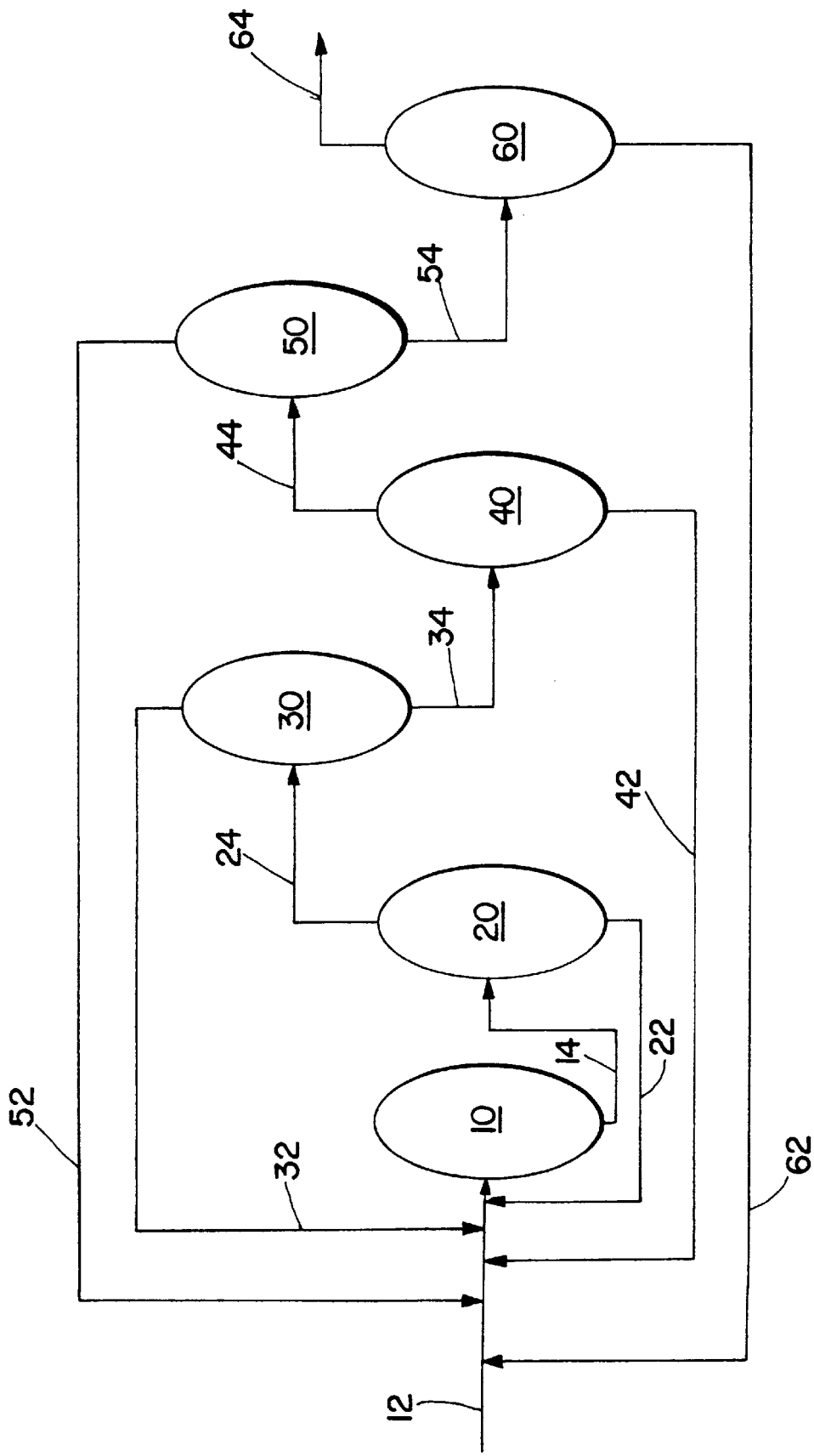
FIG. 2 shows another representative process scheme for the practice of this invention.

Still another alternative is depicted in FIG. 2. In this generalized scheme, four towers are used in series. FIG. 2 is identical to FIG. 1 except additional columns 50 and 60 are included. Instead of sending product effluent from second distillation tower 40 to first distillation tower 30 or to a separate distillation tower or towers, the effluent flows into the third distillation tower 50 via line 44. The overhead from the third distillation tower 50 is recycled to reactor 10. The third distillation bottoms is introduced into fourth distillation tower 60 via line 54. The fourth distillation bottoms is recycled to line 12 and reactor 10 via conduit 62. The final alkylene carbonate product exits the fourth distillation tower via line 64.

In general, the distillation towers (also referred to as columns) may be of conventional design. The towers may be packed with conventional packing. The temperature and pressure in the tower may be adjusted depending on the type of alkylene carbonate being produced. In general, particularly for ethylene carbonate and propylene carbonate, the tower is maintained at a temperature in the range from about 50 degrees Centigrade to about 150 degrees Centigrade, and the pressure is in the range from about 0.1 to about 100 mm Hg.

The final alkylene product produced by the process of this invention has a purity of at least 99.99 percent. Typically the final alkylene carbonate has a purity up to 100 percent and more typically more than about 99.999 percent. The final product typically has a water content less than about 20 parts per million ("ppm") and impurity levels less than 20 ppm.

It should also be appreciated that the alkylene carbonate may be made in the reactor from a variety of methods, such as from ethylene glycol and phosgene such as described in Neminowsky, *J. prakt. Chem.*, [2] 28, 3789 (1955); from diethyl carbonate and ethylene glycol by transesterification as described in Morgan et al., *J. Am. Chem. Soc.*, 75, 1263 (1053); from ethylene chlorohydrin and sodium bicarbonate as described in U.S. Pat. No. 1,907,891; or from 1,2-epoxides and carbon dioxide as described in German patent 740,366 (1943).

The process of this invention, including each sub-step of the overall process, may be operated continuously, intermittently, or as a batch process.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as illustrative embodiments. Equivalent elements or materials may be substituted for those illustrated and described herein, and certain features of the invention may be utilized independently of the use of other features, all as would be apparent to one skilled in the art after having the benefit of this description of the invention.

What is claimed is:

1. A process useful for the manufacture of alkylene carbonate, comprising:

contacting carbon dioxide, an alkylene oxide, and a carbonation catalyst in a reactor to produce a crude reactor effluent;

subjecting the crude reactor effluent to evaporation to form a first evaporator overhead containing alkylene carbonate and an evaporator bottoms stream containing the catalyst, and recycling the evaporator bottoms stream to the reactor, removing any light components present in the evaporator overhead to form a second evaporator overhead and recycling the light components to the reactor;

distilling the second evaporator overhead to form a first distillation overhead stream and a first distillation bottoms stream containing alkylene carbonate, and recycling the first distillation overhead stream to the reactor;

distilling the first distillation bottoms stream to form a second distillation overhead stream and a second distillation bottoms stream and recycling the second distillation bottoms stream to the reactor;

distilling the second distillation overhead stream to form a third distillation overhead stream and a third distillation bottoms stream and recycling the third distillation overhead stream to the reactor;

distilling the third distillation bottoms stream to form a fourth distillation overhead stream containing purified alkylene carbonate and a fourth distillation bottoms stream, and recycling the fourth distillation bottoms stream to the reactor.

2. The process of claim 1 wherein the evaporation occurs in a wiped film evaporator or a falling film tower.

3. The process of claim 1 wherein the distilling of the evaporation overhead and second distillation overhead occurs in a first distillation tower and the distilling of the first and third distillation bottoms occurs in a second distillation tower.

4. The process of claim 1 wherein each distilling is conducted under a temperature in the range of about 50 degrees Centigrade to about 150 degrees Centigrade.

5. The process of claim 1 wherein each distilling is conducted at a pressure of about 0.1 mm Hg to about 100 mm Hg.

6. The process of claim 1 wherein the alkylene carbonate is ethylene carbonate, propylene carbonate, or butylene carbonate.

7. The process of claim 1 wherein the catalyst is a tetraalkyl ammonium halide.

8. The process of claim 1 wherein the catalyst is tetraethyl ammonium bromide.

9. The process of claim 1 conducted to provide the fourth distillation overhead stream having an alkylene carbonate in a purity of at least 99.99 percent, having a water content less than 20 parts per million, and having a glycol content of less than 20 parts per million.

10. The process of claim 1 wherein the contacting in the reactor is maintained at a temperature of about 170 degrees Centigrade to about 190 degrees Centigrade.

11. The process of claim 1, wherein the alkylene carbonate is propylene carbonate.

12. The process of claim 1, wherein the alkylene carbonate is ethylene carbonate.

* * * * *